United States Patent
Holmstrom et al.

(10) Patent No.: US 11,931,599 B2
(45) Date of Patent: Mar. 19, 2024

(54) METHOD AND COMPUTER PROGRAM PRODUCT FOR DOSE MAP PREDICTION FOR RADIOTHERAPY TREATMENT PLANNING

(71) Applicant: RaySearch Laboratories AB (Publ), Stockholm (SE)

(72) Inventors: Mats Holmstrom, Värmdö (SE); David Andersson, Uppsala (SE); Gabriel Carrizo, Johanneshov (SE); Adnan Hossain, Skärholmen (SE)

(73) Assignee: Raysearch Laboratories AB (publ), Stockholm (SE)

( * ) Notice: Subject to any disclaimer, the term of this patent is extended or adjusted under 35 U.S.C. 154(b) by 0 days.

(21) Appl. No.: 18/256,427

(22) PCT Filed: Nov. 29, 2021

(86) PCT No.: PCT/EP2021/083314
§ 371 (c)(1),
(2) Date: Jun. 8, 2023

(87) PCT Pub. No.: WO2022/122442
PCT Pub. Date: Jun. 16, 2022

(65) Prior Publication Data
US 2024/0033539 A1 Feb. 1, 2024

(30) Foreign Application Priority Data
Dec. 9, 2020 (EP) .................................. 20212760

(51) Int. Cl.
*A61N 5/00* (2006.01)
*A61N 5/10* (2006.01)
*G16H 20/40* (2018.01)

(52) U.S. Cl.
CPC ......... *A61N 5/1038* (2013.01); *A61N 5/1039* (2013.01); *G16H 20/40* (2018.01)

(58) Field of Classification Search
None
See application file for complete search history.

(56) References Cited

U.S. PATENT DOCUMENTS

2016/0129282 A1* 5/2016 Yin ..................... G16H 40/20
600/1
2018/0043184 A1* 2/2018 Wu ..................... A61N 5/1077
(Continued)

FOREIGN PATENT DOCUMENTS

CN 108721792 A 11/2011
CN 108717866 A 10/2018
(Continued)

OTHER PUBLICATIONS

Ming, Ma et al., Incorporating dosimetric features into the prediction of 3D VMAT dose distributions using deep convolutional neural network Phys. Med. Biol. 64 (2019) 125017 (11pp).
(Continued)

*Primary Examiner* — Hoon K Song
(74) *Attorney, Agent, or Firm* — Noréns Patentbyrå AB

(57) ABSTRACT

An estimated or predicted dose for radiotherapy treatment may be generated based on a partial dose map including dose information only for one or more regions of interest within a treatment site, by use of a properly trained machine learning system such as a U-Net or a V-Net. Said partial dose map typically set to fulfil clinical goals. A method of training such a machine learning system is also disclosed.

16 Claims, 3 Drawing Sheets

(56) References Cited

U.S. PATENT DOCUMENTS

2020/0171325 A1 6/2020 Yang et al.
2020/0254277 A1* 8/2020 Eriksson ............. A61N 5/1039

FOREIGN PATENT DOCUMENTS

| CN | 108766563 A | 11/2018 |
| CN | 108899093 A | 11/2018 |
| CN | 109166613 A | 1/2019 |
| CN | 110085298 A | 8/2019 |
| CN | 110124214 A | 8/2019 |

OTHER PUBLICATIONS

International Search Report & Written Opinion, European Patent Office, dated Feb. 10, 2022, Rijswijk, Netherlands.
Office Action dated Nov. 13, 2023 in corresponding Chinese patent application No. 202180080293.7, Chinese Patent Office, Beijing, China.

\* cited by examiner

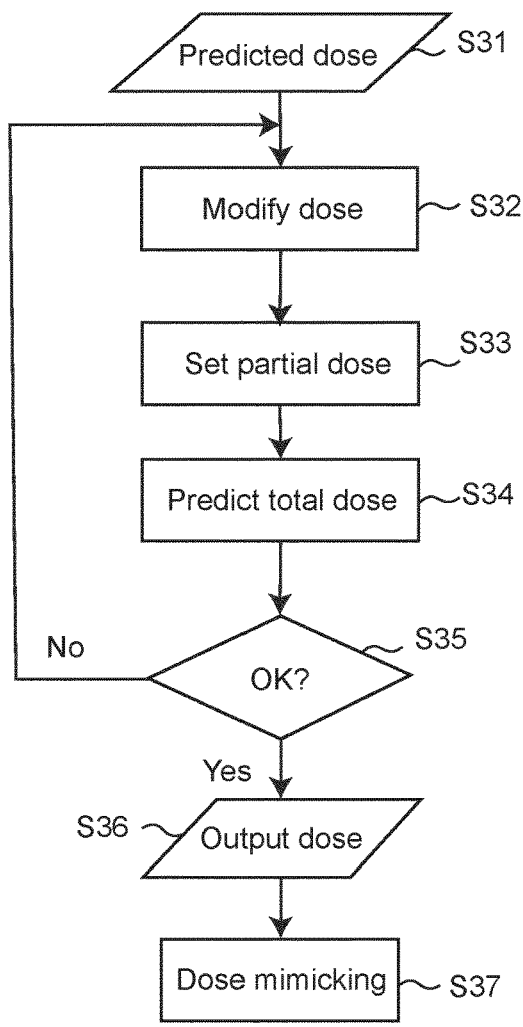
FIGURE 3
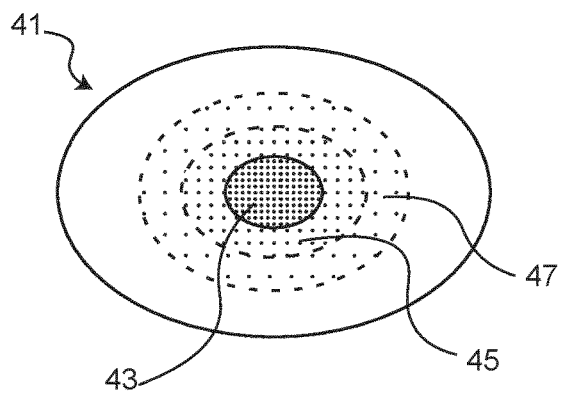
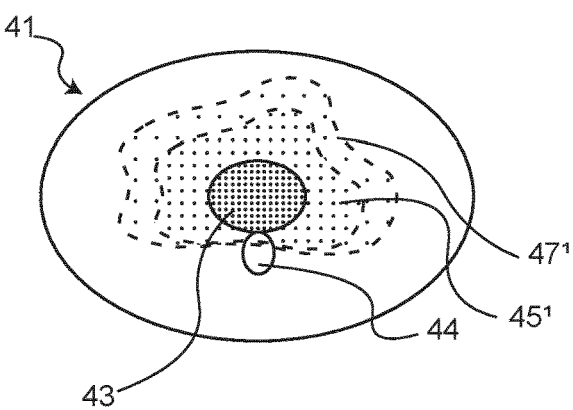
FIGURE 4a  FIGURE 4b

METHOD AND COMPUTER PROGRAM PRODUCT FOR DOSE MAP PREDICTION FOR RADIOTHERAPY TREATMENT PLANNING

TECHNICAL FIELD

The present invention relates to radiotherapy treatment planning and in particular to the prediction of dose distributions, which are sometimes alternatively referred to as dose maps.

BACKGROUND

Dose planning is key element of radiotherapy treatment planning and is based on clinical goals such as ensuring a high dose to a planning target volume (PTV) and the lowest possible dose to the surrounding organs at risk (OAR). One way of obtaining a plan is to predict a spatial dose distribution for the whole treatment site and base the plan on this predicted dose distribution. The dose that is actually delivered to the patient will differ from the predicted dose because of physical laws and the technical limitations of the delivery apparatus. It is always desirable to start plan optimization with a predicted dose distribution that is as close as possible to a realistic, physically attainable dose distribution, because this will result in a plan that is better adapted to the clinical goals. Several efforts have been made to arrive at an estimated or predicted spatial dose distribution that fulfils this requirement. It is made more difficult because a change of the desired dose in one part of the treatment site will inevitably result in a change in other parts of the treatment site.

In recent years, machine learning has been employed to produce such estimated or predicted dose distributions based on structure data obtained from images and segmented structures of the treatment site. Such methods do not always yield a satisfactory result. In particular, a change in the predicted dose in one organ or other type of region of interest may not result in appropriate changes in the predicted doses of other organs. Such a change may be made, for example, if the predicted dose distribution does not fulfil a clinical goal, for example does not reach the minimum dose prescribed for the target or the maximum dose constraint in an OAR.

Ming Ma et al., Incorporating dosimetric features into the prediction of 3D VMAT dose distributions using deep convolutional neural network Phys. Med. Biol. 64 (2019) 125017 (11pp) seeks to mitigate the problem that dose prediction methods based on segmented images sometimes result in unsatisfactory target dose, and proposes the inclusion of a dose distribution from a plan considering only the PTV, in addition to the contour data commonly used in dose planning methods. This PTV-only plan has been obtained with respect only to the target, with the aim of ensuring the best possible target dose while disregarding the desire to spare organs at risk.

SUMMARY OF THE INVENTION

The invention aims at providing a feasible estimated dose distribution for use in radiotherapy treatment planning, in particular one that closely resembles a physically deliverable dose distribution.

The invention relates to a method of training a machine learning system to generate an estimated spatial radiotherapy dose distribution for a treatment site including at least a portion of a patient to be treated comprising inputting to the machine learning system a plurality of training data sets, each training data set comprising a spatial radiotherapy dose distribution for a treatment site and a training partial radiotherapy dose distribution including dose information for one or more regions of interest within the treatment site, and evaluating the output based on the spatial radiotherapy dose distribution. The spatial radiotherapy dose distributions used in the training data sets may be obtained in any suitable way, for example as deliverable doses or computer-generated doses.

The invention also relates to a computer implemented method for generating an estimated spatial radiotherapy dose distribution for a treatment site including at least a portion of a patient to be treated, the method comprising the steps of inputting a planning partial radiotherapy dose distribution including dose information for one or more regions of interest within the treatment site to a machine learning system that has been trained according to the above, and generating, by the machine learning system, an estimated spatial radiotherapy dose distribution for the treatment site based on the planning partial radiotherapy dose distribution.

Hence, the method above enables the estimation of a full spatial dose distribution from a planning partial spatial dose distribution covering only one or more portions of the whole treatment site, without the input of structure data or other types of image data by using a trained machine learning system. The method according to the invention enables dose prediction that will enable a physically feasible predicted or estimated dose distribution based only on partial dose information regarding the treatment site. That is, image data and structural data are not needed. The planning partial dose distribution may be a deliverable dose for any type of delivery apparatus, or a synthetic dose distribution generated using any algorithm.

The training data set may further include image information and/or structure information regarding the treatment site. This will enable a more advanced model that will be able to generate a more accurate predicted dose distribution as there is a correlation between dose fall off and tissue type and structure.

Typically, for the method of generating an estimated dose distribution, the planning partial radiotherapy dose distribution is set by a human operator such as a clinician, or by an algorithm, such as a suitably trained machine-learning model, for the one or more regions of interest. The planning partial radiotherapy dose distribution may be based on a previously calculated plan for the patient, after a part of the previously calculated plan has been delivered to the patient. The step of generating the estimated dose distribution may be subject to constraints so that the dose or doses set in the planning partial dose distribution may only change within preset limits, or by a certain amount, which may be a fixed amount, or determined relative to the dose in question. Alternatively, the constraints may be set in such a way that the dose or doses set in the planning partial dose distribution may not be changed at all.

Embodiments of the method of generating an estimated dose distribution also include the step of evaluating the estimated total radiotherapy dose distribution and, depending on the result of the estimation, modifying the planning partial radiotherapy dose distribution and generating an updated estimated total radiotherapy dose distribution based on the modified planning partial radiotherapy dose distribution and outputting the updated estimated total radiotherapy dose distribution as the total dose distribution. This is particularly useful if a change has to be made between fractions of the plan, since it a simple way to provide input data for recalculation of the plan by inputting the dose distribution to the most important regions of interest.

The method of generating an estimated dose distribution may further include the step of performing dose mimicking based on the estimated or predicted spatial dose distribution. In this document the terms estimated and predicted are used interchangeably.

The input data to the machine learning system may further include information regarding machine parameters and/or beam setup of the delivery apparatus that intended to be used in dose delivery. For dose mimicking the spatial dose distribution can then be mimicked using optimization framework found in radiotherapy treatment planning systems such as RayStation®. This information may be used to improve the dose prediction, by taking into account the capabilities the delivery apparatus so that unattainable predictions may be avoided.

Advantageously, the doses included in the partial dose distribution information are selected to be the most important doses to consider, typically covering regions of interest, such as the target and one or more organs at risk for which clinical goals have been set. This applies both to the training partial dose distributions and the planning partial dose distributions.

The machine learning network used may be any deep learning system that is able to handle pixels or voxels, such as a U-Net or a V-net.

The invention also relates to a computer program product comprising computer-readable code means which, when executed in a computer will cause the computer to perform the method according to any one of the methods discussed above. The computer program product may comprise non-transitory storage medium holding the computer readable code.

The disclosure also relates to a computer comprising a processor and a program memory, said program memory being arranged to hold such a computer program product.

BRIEF DESCRIPTION OF DRAWINGS

The invention will be described in more detail in the following, by way of examples and with reference to the appended drawings.

FIG. 3 is a flow chart of a possible implementation of a method according to the invention for guided optimization.

FIGS. 4*a* and 4*b* illustrate the estimated dose at two different steps of the method in FIG. 3.

DETAILED DESCRIPTION OF EMBODIMENTS

Figure 1:
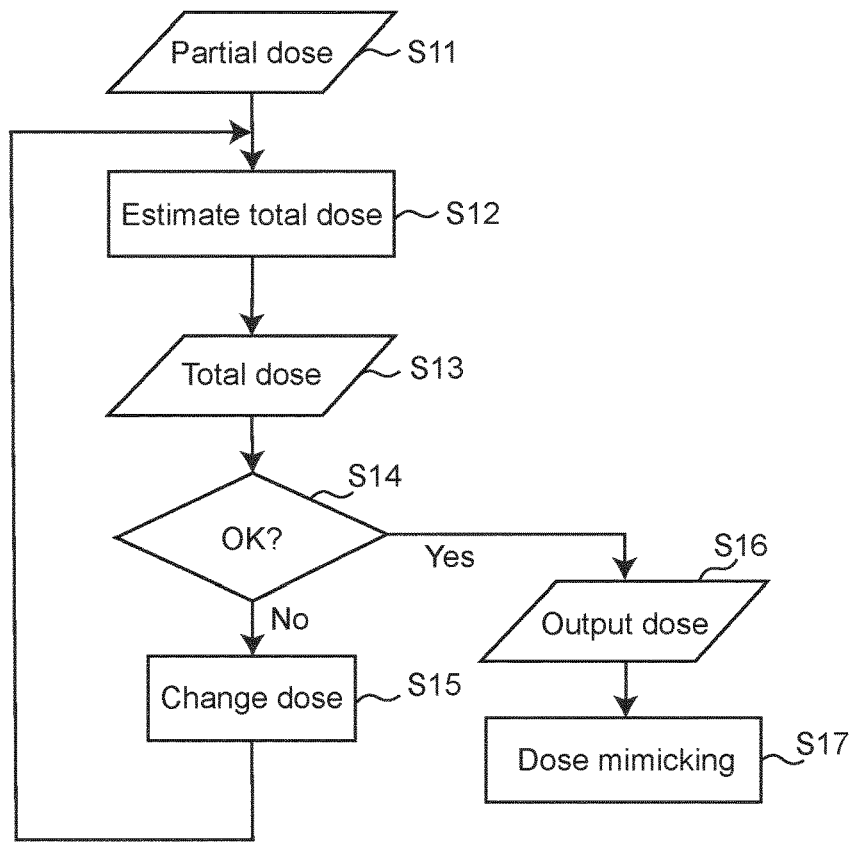
FIG. 1 is a flow chart of an embodiment of the inventive method.

FIG. 1 is a flow chart of an embodiment of the inventive method for generating a predicted or estimated dose map. In step S11, a planning partial dose distribution is set, for at least one area in the treatment site. The planning partial dose distribution may be set by a human operator such as a clinician, or by a suitably trained machine learning system, or in any other suitable way. Typically, the dose to the target and to one or more organs at risk are set. The planning partial dose distribution is input to a suitably trained machine learning system, which will be discussed in more detail below. In step S12, an estimated total dose distribution is determined by the machine learning system and is output in step S13. In step S14 the estimated total dose distribution is evaluated. The evaluation may be performed by a human operator or by an algorithm such as a suitably trained machine learning system. If the total dose distribution is found to be acceptable, it is output in step S16 and from there may be used for dose mimicking in a subsequent step S17 in the conventional way. If the estimated total dose distribution is found in step S14 to be not acceptable, the operator or algorithm, respectively, can change, in a step S15, the desired dose for an area of the treatment site and return to step S12. The machine learning system will then return, in step S13, a refined estimated total dose distribution which can again be evaluated. Throughout this document the term treatment site may refer to a portion of a patient or the whole body of the patient. In addition, the treatment site may include structures external to the patient which may affect the dose delivery, such as a couch on which the patient is positioned. It should be noted that steps S14, S15 and S16 are optional steps. If no evaluation is desired, the method can proceed directly from step S13 to step S17. In this case, the first estimated total dose distribution is used directly for dose mimicking. The estimated total dose distribution is a spatial dose distribution.

The change in S15 may be any change that is deemed feasible by the operator. for example, if target coverage is good, but the dose is too high in an OAR, such as the rectum, bladder or spinal cord, the operator may set a lower dose in that OAR. This change will affect other parts of the dose map, which is why the method must then return to step S12 for a new dose estimate which should have both good target coverage and lowered dose in the OAR. The evaluation can be extended to cover multiple areas of the treatment site to meet an arbitrary amount of evaluation criteria.

For determining the estimated dose in step S12, the amount of change allowed for the regions of interest included in the planning partial dose distribution should be restricted. In some embodiments, no change may be allowed, that is, the estimated dose distribution must have exactly the specified dose in these regions of interest. In other embodiments, a certain level of change may be allowed, within preset limits either as a fixed number of Gy, or relative to the dose in the region of interest concerned.

Figure 2:
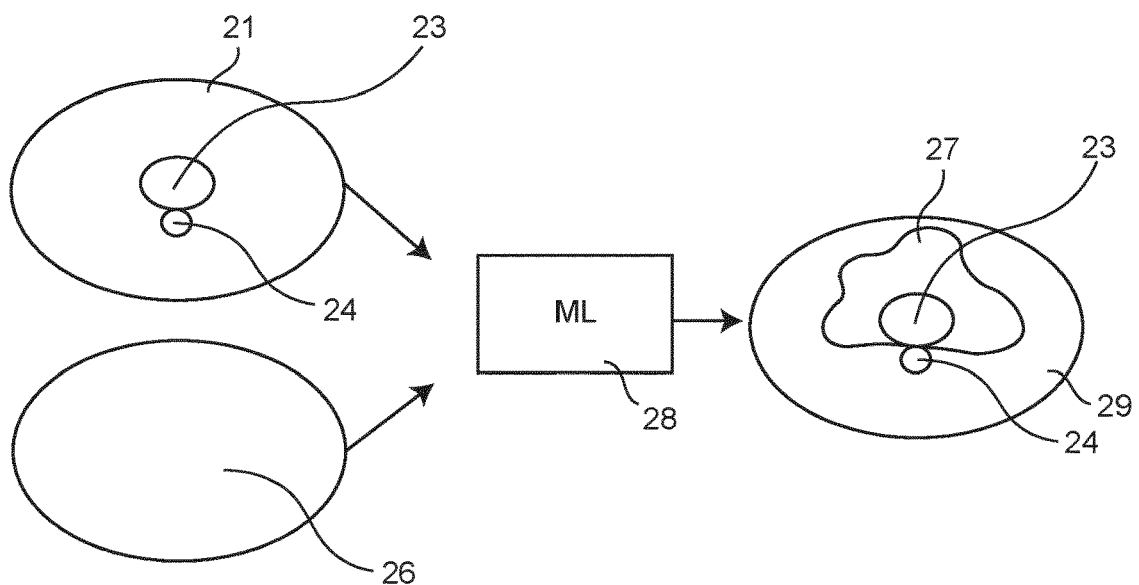
FIG. 2 illustrates schematically the structure of the method of FIG. 1.

FIG. 2 illustrates schematically the structure of the method of FIG. 1. A planning partial dose distribution 21 includes the dose of a target, in this case a prostate 23, and an organ at risk 24, in this case a rectum, which should receive as low dose as possible. The portions of the planning partial dose distribution 21 that should be considered, that is, the ones for which a dose has been set, the prostate 23 and the rectum 24, are defined by a mask. An outline 26 defines the extent of the treatment site and could also include the mask. The planning partial dose distribution 21 and the outline 26 are used as input to a machine learning system 28, which has been trained to output a total predicted dose distribution 29. The dense pattern of dots inside the area corresponding to the prostate 23 illustrates the high dose in this area. An area 27 around the prostate has a less dense pattern to illustrate that the dose in this area is lower. As will be understood, FIG. 2 is greatly simplified. A real dose distribution will normally have more different regions of interest with different doses.

The machine learning system used according to the invention may be any deep learning system that is able to handle pixels or voxels, including a U-Net or a V-net. The training data sets include training partial dose distributions and the correct complete dose distributions corresponding to the training partial dose distributions. Preferably, a wide variety of different dose distribution should be included. The training partial dose distributions can be obtained from total dose distribution by masking out areas of the total dose distribution so that only the doses in selected areas are present. The training data set may also include image data and/or structure data related to the treatment site, for increased accuracy in the dose prediction.

The training may be related to a particular region of the body, or treatment site, for example, head, neck, or abdomen for training specifically on that region. It would also be possible to train the machine learning system with respect to the whole body, depending on the availability of a sufficient amount of training data.

One specific field of application of the inventive methods is to facilitate fallback planning. Fallback planning is used when the plan has to be recalculated for use with a different delivery machine than originally planned. This may happen, for example, because there is an issue with the first machine. In such cases, the original plan will have to be updated with respect to the new machine parameters and its beam set configuration. This results in changes to the actual dose distribution because different machines have different properties. Using the method according to an embodiment of the invention, the new dose shape can be readjusted by inputting the dose for one or more regions of interest into the machine learning system as discussed above, which will output a new total dose distribution. Typically, the regions of interest will be the target and one or more organs at risk, but they may also be a part of a target or other structure, for example a portion of the target that is dangerously close to an organ at risk and therefore should not receive a full dose. This new dose distribution can be used to recalculate the plan for the new delivery machine.

The method according to embodiments of the invention may also be used in a guided optimization procedure, for example, according to the following, with reference to FIG. 3:

In step S31, a predicted dose is obtained in a suitable way. The predicted dose may, for example, be output from a machine learning system trained on plans optimized to meet target prescription with a uniform falloff.

The operator modifies the predicted dose in step S32 in one or more regions of interest based on CG (clinical goals) or optimization functions.

In step S33, modified region doses as well as targets are set as a planning partial dose distribution, and in step S34, the partial model is used to predict a new spatial dose distribution. The partial models have been trained on multiple plans with different tradeoffs and augmented doses. In step S35, the new predicted dose distribution is reviewed, by the human operator or by a suitable algorithm. If the new predicted dose distribution is ok, the total dose distribution is output in step S36 and the process proceeds to dose mimicking S37 using input from clinical goals and optimization functions, and external dose outside the regions of interest. If the new predicted dose distribution is not good enough, the operator may add more clinical goals and optimization functions by going back to step S32.

An advantage of the dose planning method of FIG. 3 is that the users/clinic will not have to train their own models. The dose used as input will ensure that the user's clinical input is adapted directly without the need for a specific model.

FIGS. 4a and 4b illustrate, by way of a simplified example, the steps of the method of FIG. 3. FIG. 4a is an example of step S11, showing a treatment site 41 of a patient, where the predicted dose is based on a planning partial dose set only for the target, in this example the prostate 43. As illustrated, the dose will fall of uniformly outside of the prostate 43, being lower in a first area 45 immediately surrounding the prostate 43, and even lower in a second area 47 surrounding the first area 45. The first and second areas 45, 47 are shown delimited by dashed lines. While this dose distribution provides a satisfactory target coverage, it will result in an unacceptably high dose in organs at risk that are located close to the prostate, which include the rectum and the bladder. In this example, for simplicity, only the rectum is considered.

In FIG. 4b, therefore, a dose for an area 44 corresponding to the rectum is set to zero, to ensure protection of the rectum. The resulting total dose distribution based on the dose for the target region 43 and the rectum 44, shown schematically, is reduced in the rectum area 44, which leads to increased doses in parts of the first and second areas 45', 47' surrounding the prostate 43.

Figure 5:
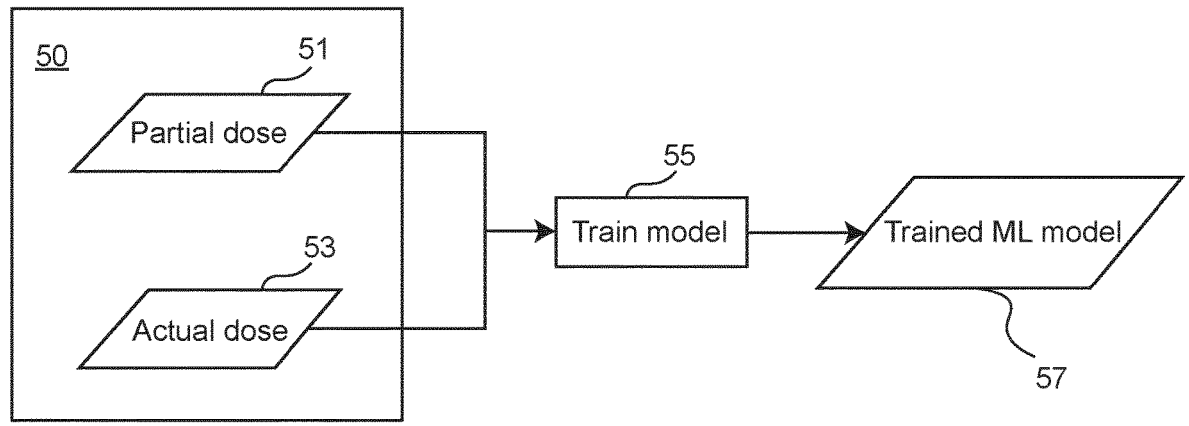
FIG. 5 shows an overall method of training the machine learning system.

FIG. 5 is an overall method of training the machine learning system to perform the inventive methods. Input data include several training sets 50 based on actual dose distributions resulting from dose planning. Each training set includes a training partial dose distribution 51 and the actual total dose distribution 53 of which it is a part. The training partial dose distribution 51 includes the dose in one or more regions of interest within the treatment site, selected from the actual total dose distribution 53. The training, in 55, includes evaluating the output from the machine learning system by comparing the output based on a training partial dose distribution to the actual dose distribution from the same training set. The result of the training is trained machine learning model 57.

Figure 6:
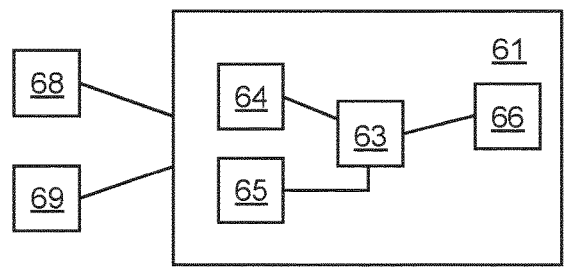
FIG. 6 is a schematic overview of a computer system in which embodiments of the invention may be implemented.

FIG. 6 is a schematic illustration of a computer system in which the method according to embodiments of the invention may be performed. A computer 61 comprises a processor 63, one or more data memories 64, 65 and one or more program memories 66. Preferably, a user input means 67, 68 is also present, in the form of a keyboard, a mouse, a joystick, voice recognition means or any other available user input means. The user input means may also be arranged to receive data from an external memory unit. It should be understood that FIG. 6 is only provided to illustrate different components that may be used to implement the method according to the invention and that the actual computer architecture can vary. One or more of the components, or the whole system, may be implemented in a cloud environment.

For refining the dose prediction, the input data may also include information regarding machine parameters and/or beam setup for the delivery apparatus. Alternatively or in addition to this, the input data set may further include image data and/or structure data related to the treatment site.

The data memory 64, 65 typically comprises the necessary input data, including the partial dose information and the output data from the dose prediction step. The input data may be generated in the computer 61, or received from another storage means, or by means of user input, in any way known in the art. As will be understood, the data memory 64 is only shown schematically. There may be several data memory units, each holding one or more different types of data, for example, one data memory for the input data, one for the dose distribution or irradiation parameters, etc.

The program memory 66 holds a machine learning system as discussed above and preferably also a dose mimicking program. As will be understood, the data memory 64, 65 and/or program memory 66 are not necessarily part of the same computer as the processor 63, and may be located in any computer that is reachable from the processor, such as in a cloud environment.

The invention claimed is:

1. A method for training a machine learning system to generate an estimated spatial radiotherapy dose distribution for a treatment site including at least a portion of a patient to be treated comprising inputting to the machine learning system a plurality of training data sets, each training data set comprising an actual spatial radiotherapy dose distribution for a treatment site and a training partial radiotherapy dose distribution, which is a part of the actual spatial radiotherapy dose distribution including dose information only for one or more regions of interest within the treatment site, and evaluating the output based on the actual spatial radiotherapy dose distribution.

2. The method of claim 1, wherein the training data set also includes image data and/or structure data related to the treatment site.

3. A computer implemented method for generating an estimated spatial radiotherapy dose distribution for a treatment site including at least a portion of a patient to be treated, the method comprising the steps of inputting a planning partial radiotherapy dose distribution including dose information for one or more regions of interest within the treatment site to a machine learning system that has been trained according to claim 1, and generating, by the machine learning system, an estimated spatial radiotherapy dose distribution for the treatment site based on the planning partial radiotherapy dose distribution.

4. The method of claim 3, wherein the planning partial radiotherapy dose distribution is set by a human operator such as a clinician for the one or more regions of interest.

5. The method of claim 3, wherein the planning partial radiotherapy dose distribution is determined based on a previously calculated plan for the patient, after a part of the previously calculated plan has been delivered to the patient.

6. The method of claim 3, wherein the step of generating an estimated spatial radiotherapy dose distribution for the treatment site includes maintaining the dose information from the planning partial dose information.

7. The method of claim 3, wherein the step of generating an estimated spatial radiotherapy dose distribution for the treatment site includes allowing the dose distribution in the one or more regions of interest to deviate from the dose information from the planning partial dose information only within certain limits.

8. The method of claim 3, further comprising the step of evaluating the estimated spatial radiotherapy dose distribution and, depending on the result of the estimation, modifying the planning partial radiotherapy dose and generating an updated estimated spatial radiotherapy dose distribution based on the modified planning partial radiotherapy dose and outputting the updated estimated spatial radiotherapy dose distribution as the total dose.

9. The method of claim 3, further comprising the step of performing dose mimicking based on the estimated spatial radiotherapy dose distribution.

10. The method of claim 3, wherein the input data set further includes information regarding machine parameters and/or beam setup for a delivery apparatus to be used when delivering the radiotherapy.

11. The method of claim 3, wherein the input data set further includes image data and/or structure data related to the treatment site.

12. The method of claim 1, wherein the one or more regions of interest includes a target.

13. The method of claim 12, wherein the one or more regions of interest includes one or more organs at risk.

14. The method of claim 1, wherein the machine learning system is a U-Net or a V-Net.

15. A computer program product comprising computer-readable code means which, when executed in a computer will cause the computer to perform the method according to claim 3.

16. A computer comprising a processor and a program memory, the program memory being arranged to hold a computer program product according to claim 15.

* * * * *